(12) United States Patent
Hansson

(10) Patent No.: US 8,043,700 B2
(45) Date of Patent: Oct. 25, 2011

(54) BICOMPONENT SUPERABSORBENT FIBRE

(75) Inventor: Charlotta Hansson, Göteborg (SE)

(73) Assignee: SCA Hygiene Products AB, Goteborg (SE)

( * ) Notice: Subject to any disclaimer, the term of this patent is extended or adjusted under 35 U.S.C. 154(b) by 176 days.

(21) Appl. No.: 12/447,729

(22) PCT Filed: Dec. 22, 2006

(86) PCT No.: PCT/SE2006/001499

§ 371 (c)(1),
(2), (4) Date: Apr. 29, 2009

(87) PCT Pub. No.: WO2008/079059

PCT Pub. Date: Jul. 3, 2008

(65) Prior Publication Data

US 2010/0003517 A1    Jan. 7, 2010

(51) Int. Cl.
*D02G 3/00* (2006.01)
(52) U.S. Cl. ........ 428/370; 428/373; 428/374; 264/168; 264/172.14; 264/210.8; 264/211.14
(58) Field of Classification Search .................. 428/370, 428/373, 374; 604/368; 264/168, 172.14, 264/172.15, 178 F, 210.8, 211.14, 232, 343
See application file for complete search history.

(56) References Cited

U.S. PATENT DOCUMENTS

| | | | | |
|---|---|---|---|---|
| 2,439,815 A | * | 4/1948 | Sisson | 428/370 |
| 3,038,236 A | * | 6/1962 | Breen | 442/200 |
| 3,038,237 A | * | 6/1962 | Taylor, Jr | 428/370 |
| 3,039,524 A | * | 6/1962 | Belck et al. | 428/374 |
| 3,864,447 A | * | 2/1975 | Sekiguchi et al. | 264/168 |
| 4,043,952 A | | 8/1977 | Ganslaw et al. | |
| 5,409,765 A | | 4/1995 | Boettcher et al. | |
| 5,998,025 A | | 12/1999 | Kido et al. | |
| 6,342,298 B1 | | 1/2002 | Evans et al. | |
| 6,610,898 B1 | | 8/2003 | Magnusson et al. | |
| 7,812,082 B2 | * | 10/2010 | McIntosh et al. | 524/492 |
| 7,838,569 B2 | * | 11/2010 | Flohr et al. | 522/4 |
| 2004/0043214 A1 | | 3/2004 | Topolkaraev et al. | |

(Continued)

FOREIGN PATENT DOCUMENTS

EP    0 248 963 A2    12/1987

(Continued)

OTHER PUBLICATIONS

Form PCT/IPEA/409 (International Preliminary Report on Patentability) issued Feb. 20, 2009 in International Application No. PCT/EP2006/001499.

(Continued)

*Primary Examiner* — N. Edwards
(74) *Attorney, Agent, or Firm* — Buchanan Ingersoll & Rooney PC

(57) ABSTRACT

A multicomponent superabsorbent fiber includes a first superabsorbent material and a second superabsorbent material. In at least a part of the length direction (L) of the superabsorbent fiber, the first superabsorbent material and the second superabsorbent material are located side-by-side in the cross-direction (C) of the superabsorbent fiber. The first and second superabsorbent materials are selected such that at a given point during their swelling, the swelling capacity (SC) of the first superabsorbent material is greater than the swelling capacity of the second superabsorbent material so that the superabsorbent fiber (10) curls upon contact with liquid. Also, a method for reducing gel-blocking in a superabsorbent fiber.

11 Claims, 5 Drawing Sheets

U.S. PATENT DOCUMENTS

| | | |
|---|---|---|
| 2005/0130540 A1 | 6/2005 | Crane |
| 2005/0204500 A1 | 9/2005 | Mikula |
| 2006/0178071 A1* | 8/2006 | Schmidt et al. ............... 442/417 |

FOREIGN PATENT DOCUMENTS

| | | |
|---|---|---|
| EP | 0 343 941 A2 | 11/1989 |
| EP | 1 594 557 A1 | 11/2005 |
| GB | 896955 | 5/1962 |
| JP | 2005-113135 A | 4/2005 |
| JP | 2006-097157 A | 4/2006 |
| WO | WO 01/06047 A1 | 1/2001 |
| WO | WO 2004/017883 A1 | 3/2004 |
| WO | WO 2004/069293 A1 | 8/2004 |
| WO | WO 2004/093931 A1 | 11/2004 |

OTHER PUBLICATIONS

Form PCT/ISA/210 (International Search Report) dated Aug. 7, 2007.

Form PCT/ISA/237 (Written Opinion of the International Searching Authority) dated Aug. 7, 2007.

* cited by examiner

BICOMPONENT SUPERABSORBENT FIBRE

TECHNICAL FIELD

The present invention relates to superabsorbent fibres for use in absorbent articles. The fibres are designed so that—upon contact with liquid—they provide an open structure which reduces gel blocking.

BACKGROUND OF THE INVENTION

It is known to use superabsorbent materials, (often superabsorbent polymers, SAP) in disposable absorbent products such as diapers, incontinence guards, sanitary napkins, panty liners and the like for absorbing e.g. urine, menses or liquid from faeces etc. Superabsorbent materials can absorb liquid in amounts which are usually several times the mass of the polymers themselves. Superabsorbent polymers are sometimes called hydrogels or gels.

Upon absorbing liquid, superabsorbent materials tend to swell. However, this can lead to a phenomenon known as "gel blocking" in which the part of the superabsorbent material which first makes contact with liquid expands and prevents liquid from penetrating further into the remainder of the superabsorbent material. Gel blocking is particularly a problem for absorbent articles which contain relatively large concentrations of superabsorbent material and which are designed to absorb relatively large amounts of liquid.

There have been a number of attempts to eliminate or overcome the problem of gel blocking. Strategies include adapting the chemical composition, distribution or concentration of the superabsorbent material itself, mixing other absorbent materials with the superabsorbent material or including additional layers of material in the absorbent article which function as reservoirs. Examples can be found in EP 0 343 941, EP 1 594 557, JP 2005 113135 and WO 2004/093931.

U.S. Pat. No. 6,342,298 describes multicomponent superabsorbent fibers which comprise at least one acidic water-absorbing resin and at least one basic water-absorbing resin. The acidic and basic resins are in close proximity so as to maximize ion exchange between the two.

US 2005/0130540 discloses a nonwoven web of multicomponent filaments. The filaments comprise superabsorbent polymer in their centre surrounded by a thermoplastic polymer sheath.

U.S. Pat. No. 6,610,898 describes the use of heat-shrunk, spiralized thermoplastic multicomponent fibres to provide an open and lofty structure in a fluid acquisition/transfer layer of an absorbent article.

WO 2004/017883 discloses an absorbent core which contains fibres coated with SAP. Some or all fibres may be only partially covered with SAP.

There remains a need, however, for simple ways in which gel blocking can be reduced. In particular, there is a need for novel superabsorbent materials which can be readily produced from known technologies, which can be manufactured from existing materials and which reduce or eliminate the problems associated with gel blocking. In addition, it is often desirable to create open structures based on superabsorbent polymers. Dynamic systems which change their physical structure, or are activated upon absorbing liquid, are also desirable.

SUMMARY OF THE INVENTION

The present invention relates to a multicomponent superabsorbent fibre. The superabsorbent fibre has a length direction (L) and a cross-direction (C), and comprises a first superabsorbent material and a second superabsorbent material. At least a part of the length direction (L) of the superabsorbent fibre, the first superabsorbent material and the second superabsorbent material are located side-by-side in the cross-direction (C) of the superabsorbent fibre. The first and second superabsorbent materials are selected such that—at a given point during their swelling—the swelling capacity (SC) of the first superabsorbent material is greater than the swelling capacity (SC) of the second superabsorbent material so that the superabsorbent fibre curls upon contact with liquid.

Due to the difference between the swelling capacity of the first and second superabsorbent materials—exposure of the superabsorbent fibre to liquid makes one superabsorbent material swell more than the other superabsorbent material. This in turn exerts physical forces on the superabsorbent fibre which cause it to expand unevenly, thus curling. Curled fibres provide a lower density, more open interfibre structure around the superabsorbent fibre, thus allowing liquid to penetrate better into the structure and reducing gel-blocking.

Multicomponent superabsorbent fibres comprising one or more first fibres comprising an acidic water-absorbent resin and one or more second fibres comprising a basic water-absorbent resin are not included in the scope of the present invention.

The superabsorbent fibre may be a bicomponent fibre consisting of the first superabsorbent material and the second superabsorbent material.

In one embodiment, the first superabsorbent material and the second superabsorbent material may comprise the same superabsorbent polymer, wherein the superabsorbent polymer in the second superabsorbent material has a higher cross-linking density than the superabsorbent polymer in the first superabsorbent material.

The first superabsorbent material and the second superabsorbent material may have the same total swelling capacity (TSC) yet different swelling rates (SR).

According to another aspect the first superabsorbent material has a total swelling capacity (TSC) which is at least 1.1 times, such as at least 1.5 times, at least 2 times or at least 3 times greater than, that of the second superabsorbent material.

Suitably, the first and second superabsorbent materials are arranged such that there is at least one plane or axis of asymmetry in the length direction (L) of the superabsorbent fibre.

The present invention also provides to an absorbent core comprising the multicomponent superabsorbent fibres of the invention and an absorbent article comprising such an absorbent core.

The present invention also relates to a method for reducing gel-blocking around a superabsorbent fibre. The method comprises; providing a multicomponent superabsorbent fibre having a length direction (L) and a cross-direction (C), said superabsorbent fibre comprising a first superabsorbent material and a second superabsorbent material. In at least a part of the length direction (L) of the fibre, the first superabsorbent material and the second superabsorbent material are located side-by-side in the cross-direction (C) of the superabsorbent fibre. The first and second superabsorbent materials are selected such that—at a given point during their swelling—the swelling capacity (SC) of the first superabsorbent material is greater than the swelling capacity (SC) of the second superabsorbent material. The method further comprises exposing the superabsorbent fibre to liquid, wherein—at a given point during their swelling—the swelling capacity (SC) of the first superabsorbent material (20) is greater than the swelling capacity (SC) of the second superabsorbent material (30), causing the bicomponent superabsorbent fibre to curl.

DETAILED DESCRIPTION OF PREFERRED EMBODIMENTS

Figure 1A:
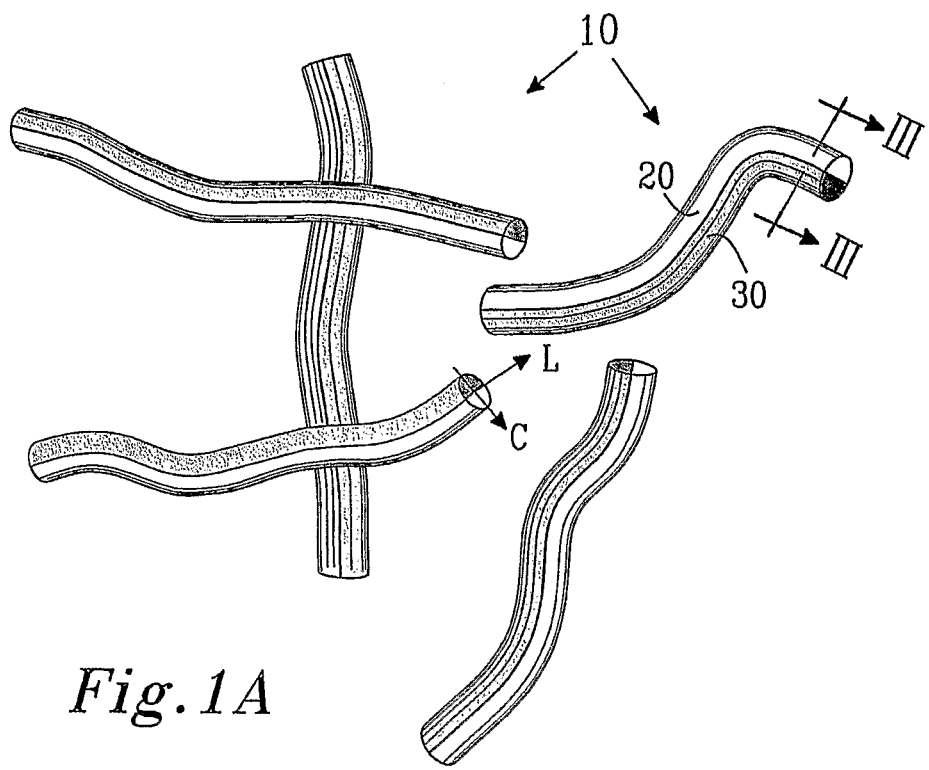
FIG. 1 shows a first embodiment of the invention.
Figure 1B:
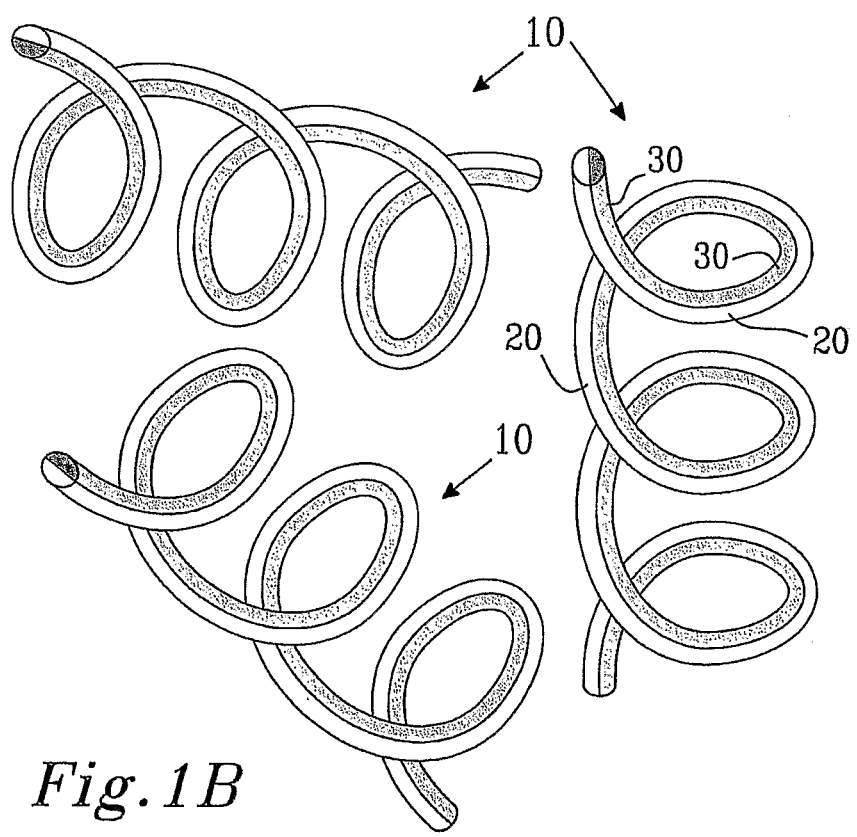

FIGS. 1A and 1B show the multicomponent superabsorbent fibre 10 according to the invention, before and after liquid absorption, respectively.

The fibre 10 is a multicomponent fibre. In other words, it is made up of one or more essentially unitary materials which are not closely intermixed. Although the boundaries between the components of the fibre 10 may not be well-defined due to chemical or physical interaction between the components (e.g. co-melting, co-mingling or diffusion), there exists a region or regions of the fibre 10 which consist primarily of one component. The following discussion concerns primarily bicomponent fibres 10, however, this should be understood as a specific embodiment of the invention, and should not be considered as limiting. Fibres 10 which comprise three, four or more components are also conceivable.

The fibre 10 is superabsorbent—i.e. it is made from superabsorbent materials—materials which can absorb liquid in amounts many times their own weight. In this way, it differs from the pulp fibres, fibres from natural sources or synthetic fibres which are often used in absorbent articles. Suitably, the fibre 10 only comprises superabsorbent materials, and does not comprise other types of fibrous materials.

The multicomponent superabsorbent fibre 10 has a length direction (L) which is parallel to its major axis of the fibre 10 when the fibre 10 is drawn out to its full extent. Typically, superabsorbent fibres 10 according to the present invention have a total length of between 3 mm and 10 cm when drawn out to their full extent.

The superabsorbent fibre 10 also has a cross-direction (C) which lies perpendicular to the length direction (L). Typically, superabsorbent fibres 10 according to the present invention have a maximum thickness in the cross-direction of between 10 μm and 200 μm, preferably between 200 μm and 100 μm. The superabsorbent fibre need not have a circular cross-section; cross-sectional areas which are square, rectangular, triangular, oval, star-shaped or irregular-shaped are also within the scope of the present invention.

The superabsorbent fibre 10 comprises a first superabsorbent material 20 and a second superabsorbent material 30. In a preferred embodiment (FIG. 1A), the superabsorbent fibre 10 consists solely of a first superabsorbent material 20 and a second superabsorbent material 30.

Superabsorbent materials which can be used in the present invention are suitably superabsorbent polymers (SAPs). SAPs are usually cross-linked hydrophilic polymers, and may be based on polyacrylates, polystyrenes, polyacrylamides, polyvinylalcohols, polyvinyl ethers, polyethylene oxides, polyvinyl pyridines, polyvinylpyrrolydones, polyvinyl morpholinones and polyacrylonitriles. Such polymers may also have a natural source; e.g. hydrolysed starch acrylonitrile polymers, substituted cellulose polymers (e.g. carboxymethylcellulose, CMC, hydroxypropyl cellulose or carboxymethyl starch). The polymers may be substituted or unsubstituted. Further SAPs are N,N-dimethylaminoethyl or N,N-diethylaminopropyl acrylates and methacrylates, and the respective quaternary salts thereof. Typically, superabsorbent polymers useful in the present invention have a multiplicity of anionic, functional groups, such as sulfonic acid, and more typically carboxy, groups. A particularly preferred SAP is based on the cross-linked co-polymer of acrylic acid and acrylate monomers. Olefinically unsaturated carboxylic acid and carboxylic acid anhydride monomers include the acrylic acids typified by acrylic acid itself, methacrylic acid, ethacrylic acid, di-chloroacrylic acid, cyanoacrylic acid, methylacrylic acid (crotonic acid), aphenylacrylic acid, ss-acryloxypropionic acid, sorbic acid, a-chlorosorbic acid, angelic acid, cinnamic acid, p-chlorocinnamic acid, sterylacrylic acid, itaconic acid, citroconic acid, mesaconic acid, glutaconic acid, aconitic acid, maleic acid, fumaric acid, tricarboxyethylene and maleic acid anhydride. Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2hydroxy-3-methacryloxypropyl sulfonic acid and 2-acrylamide-2-methylpropane sulfonic acid.

The SAP is preferably cross-linked, so as to reduce its solubility in water. Cross-linking may occur in the bulk of the SAP (bulk cross-linking), or on the surfaces of SAP particles (surface cross-linking). Bulk cross-linking agents are commonly branched molecules containing at least two polymerisable groups, usually three polymerisable groups. Cross-linking agents may be prepared by functionalising a core molecule (e.g. polyalcohols such as glycol or polyamines such as diethylenetriamine) with functional groups which can be incorporated into the SAP. Divinyl benzene, acryloyl or methacrylyl polyesters of polyhydroxylated compounds, divinyl esters of polycarboxylic acid, diallyl esters of polycarboxylic acids, diallyl dimethyl ammonium chloride, triallyl terephthalate, methylene bisacrylamide, diallyl maleate, diallyl fumarate, hexamethylene bis maleimide, triallyl phosphate, trivinyl trimellitate, divinyl adipate, glyceryl trimethacrylate, diallyl succinate, divinyl ether, the divinyl ethers of ethylene glycol or diethylene glycol diacrylate, polyethylene glycol diacrylates or methacrylates, 1,6-hexanediol diacrylate, pentaerythritol triacrylate or tetracrylate, neopentyl glycol diacrylate, cyclopentadiene diacrylate, the butylene glycol diacrylates or dimethyacrylates, trimethylolpropane di- or tri-acrylates are all examples of cross-linking agents. The cross-linking agents may be present in amount of between 0-5 mol %.

Surface crosslinking involves that the superabsorbent easier maintains its original shape also when exerted to external loads and after several wettings. Surface crosslinking of the superabsorbent is usually made by esterification of carboxylic acid groups. One example of surface crosslinking agents is polyhydroxy substances. Another example is organic carbonates, preferably ethylene carbonate in aqueous solution. A third example is the use of diglycidyl compounds, especially etherlene glycol-diglycidyl ether (EDGE). It is also known through e.g. U.S. Pat. No. 4,043,952 to surface crosslink a superabsorbent based on an anionic polyelectrolyte with a polyvalent metal ion, e.g. aluminium. The surface crosslinking occurs with ionic bonds. Through EP 0 248 963 it is known to surface crosslink a superabsorbent of anionic character with a polyquaternary amine for increasing the absorption capacity of the superabsorbent. Polyamines and diamines may also be used as surface crosslinkers.

The cross-sectional shape of the first and second superabsorbent materials 20, 30 is not highly relevant, and may vary along the length of the superabsorbent fibres 10. For example, the first and second superabsorbent materials 20, 30 may each individually or both together have a cross-sectional area which is circular, square, rectangular, triangular, oval or irregular-shaped. FIG. 1A shows superabsorbent fibres with a circular cross-section.

In at least a part of the length direction (L) of the superabsorbent fibre 10, the first superabsorbent material 20 and the second superabsorbent material 30 are located side-by-side in the cross-direction (C) of the superabsorbent fibre 10.

Figure 2A:
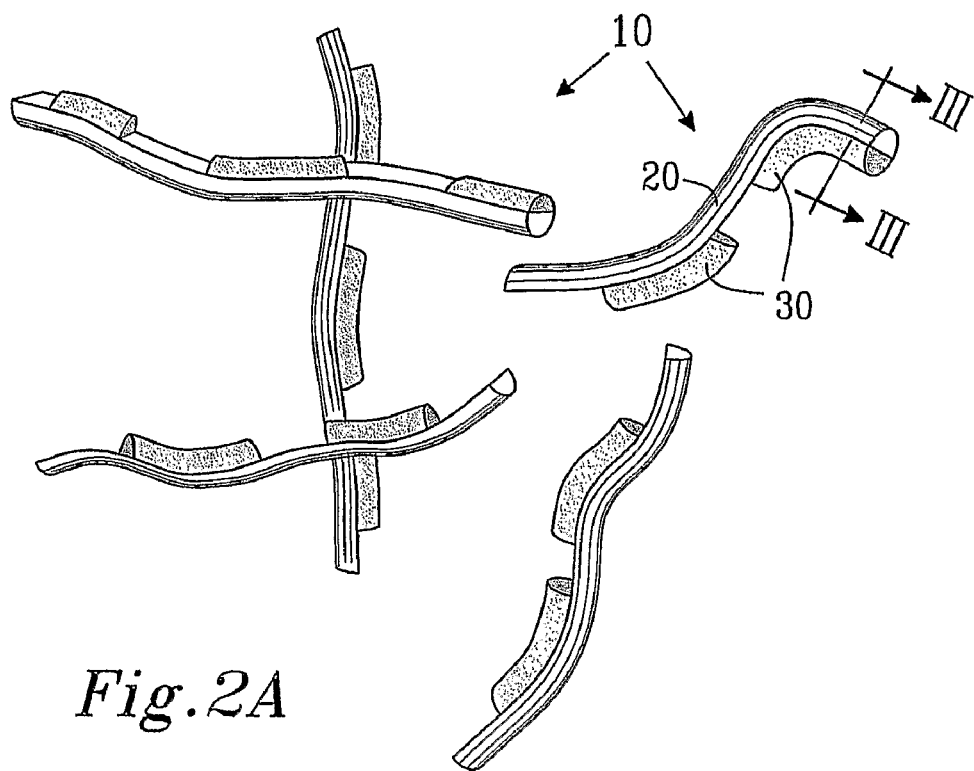
FIG. 2 shows a second embodiment of the invention.
Figure 2B:
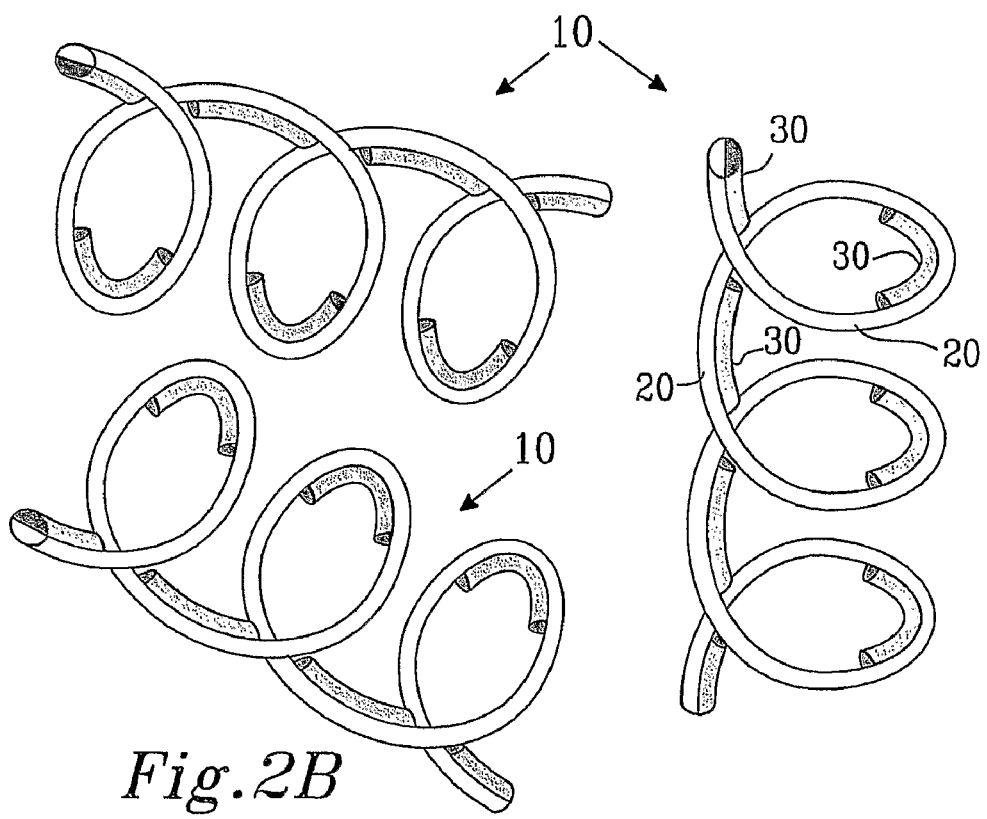

The first and second superabsorbent materials 20, 30 need not be located side-by-side in the cross-direction (C) along the entire length of the superabsorbent fibre 10, although they may be. Instead, as shown in FIGS. 2A and 2B, it may be sufficient that they are located side-by-side in only portions of the length of the superabsorbent fibre 10.

The expression "side-by-side" in the present invention means that a cross-section of the superabsorbent fibre 10 discloses both the first superabsorbent material 20 and the second superabsorbent material 30, in those lengths of the superabsorbent fibre 10 where both superabsorbent materials 20,30 are located. The first superabsorbent material 20 and the second superabsorbent material 30 need not be in contact with each other over the entire cross-section of the superabsorbent fibre 10, and need not have the same surface area in the cross-section of the superabsorbent fibre 10. A fuller understanding of the expression "side-by-side" will be gained from FIGS. 3a-3e which illustrate different embodiments of the invention in a cross-sectional view along the line III-III in FIGS. 1A and 2A.

Figure 3A:
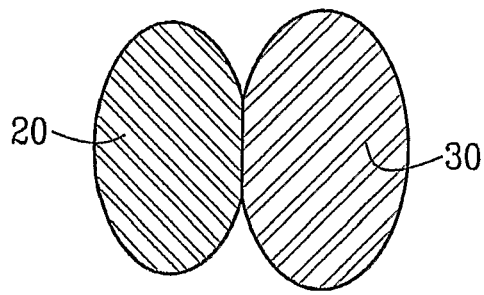
FIGS. 3a-3e are cross-sectional views through the line III-III in FIGS. 1A and 2A.

FIG. 3A shows one embodiment in which the first and second superabsorbent materials 20, 30 have an elliptical cross-section and are interconnected along a part of their common surface.

Figure 3B:
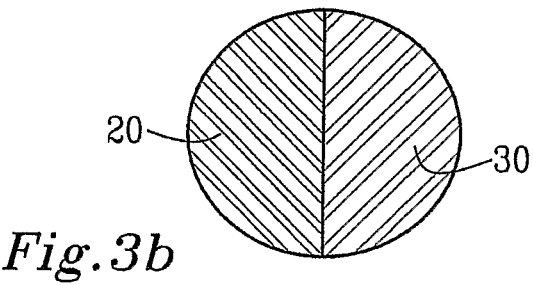

FIG. 3B shows an embodiment in which the superabsorbent fibre 10 has a substantially circular cross-section and where the first superabsorbent material 20 and the second superabsorbent material 30 have substantially semicircular cross-sections and are joined along their flat surfaces.

Figure 3C:
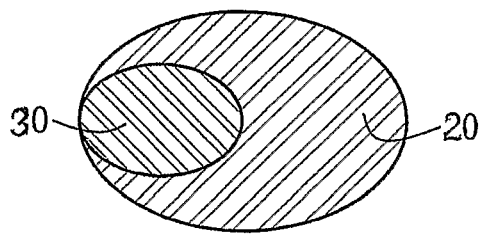

FIG. 3C shows a bicomponent superabsorbent fibre 10 in which both the first superabsorbent material 20 and the second superabsorbent material 30 have a circular cross-section and in which the first superabsorbent material 20 is eccentrically located within the second superabsorbent material 30. For best effect, the first superabsorbent material 20 is not completely enclosed within the second superabsorbent material 30, but has a surface which is coterminous with the surface of the superabsorbent fibre 10. In this way, liquid can enter the first superabsorbent material 20 without having first to pass through the second superabsorbent material 30.

Figure 3D:
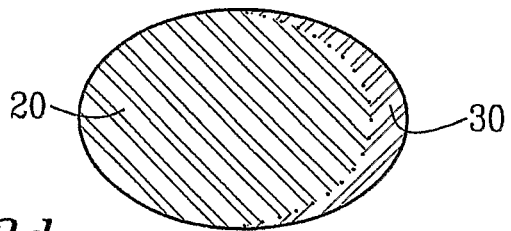

FIG. 3D shows a bicomponent superabsorbent fibre 10 in which the first superabsorbent material 20 and the second superabsorbent material 30 comprise the same superabsorbent polymer, but wherein the superabsorbent polymer which comprises the second superabsorbent material 30 has a higher cross-linking density than the superabsorbent polymer in the first superabsorbent material 20. A higher cross-linking density will tend to decrease the total swelling capacity of a superabsorbent material, while possibly increasing the swelling rate. This embodiment is easy to manufacture, as a cross-linking agent can be sprayed or coated onto one surface of a superabsorbent polymer fibre, thus forming the second superabsorbent material 30. Other methods for adjusting the swelling properties of a superabsorbent polymer can also be used to promote differential swelling and hence curling, e.g. adjusting the degree of neutralisation.

Figure 3E:
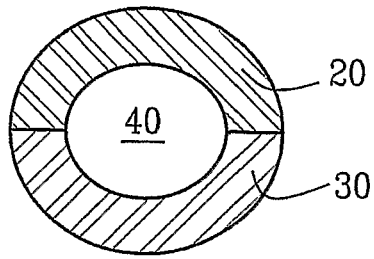

FIG. 3E shows a bicomponent superabsorbent fibre 10 having a hollow structure. The first superabsorbent material 20 and the second superabsorbent material 30 form a fibre 10 with a torus (donut-shaped) cross-section. The superabsorbent material 20, 30 therefore have a semicircular cross-section and are connected at their ends to form the fibre 10 comprising a hollow space 40 in the centre, as illustrated. The hollow space 40 may have any shape or size, and should not be considered as limited to what is illustrated.

In addition to the embodiments illustrated, other variations in the structure of the multicomponent superabsorbent fibre 10 are possible. The multicomponent superabsorbent fibre 10 may comprise more than two superabsorbent materials 20, 30. For example, a layer structure is possible, where the superabsorbent materials are stacked in the cross-direction (C). The multicomponent superabsorbent fibre 10 may also have a lobe-type cross-section, of e.g. 3, 4, 5 or more lobes, in which each lobe comprises a different superabsorbent material 20, 30. It is important in fibres having such cross-sections that there exists at least one plane or axis of asymmetry in the swelling capacity in the length direction (L) of the superabsorbent fibre.

When two or more superabsorbent materials 20, 30 are used in the multicomponent superabsorbent fibre 10, some of the superabsorbent materials 20, 30 may be the same material, provided that at least one of the superabsorbent materials 20, 30 has different swelling properties. For instance, a tri-component superabsorbent fibre 10 may comprise two superabsorbent materials which have the same SC and a third which has a different swelling capacity. In this way, great variations in the structure can be obtained, which can be adapted to suit the particular requirements of the absorbent article.

The superabsorbent materials 20, 30 should be arranged such that there is at least one plane or axis of asymmetry which lies in the length direction (L) of the superabsorbent fibre. This means that the superabsorbent materials 20, 30 should not be arranged totally symmetrically in the superabsorbent fibre 10. This maximises the curling effect of the fibre 10 upon contact with liquid.

The first and second superabsorbent materials 20, 30 are selected such that—at a given point during their swelling—the swelling capacity (SC) of the first superabsorbent material 20 is greater than the swelling capacity (SC) of the second superabsorbent material 30 so that the superabsorbent fibre 10 curls upon contact with liquid.

Before contact with liquid, the superabsorbent fibre 10 is not highly curled, as shown in FIG. 1a. However—as the swelling capacity (SC) of the first superabsorbent material 20 is greater than the swelling capacity (SC) of the second superabsorbent material 30—exposure of the superabsorbent fibre 10 to liquid makes one superabsorbent material swell faster or to a greater extent than the other superabsorbent material. This in turn exerts physical forces on the superabsorbent fibre 10 which cause it to expand unevenly, thus curling (see FIG. 1b). In their curled form, the fibres 10 pack less closely, providing a lower density, more open structure. This allows liquid to penetrate deeper into and between the fibres 10, as it flows in the spaces between the fibres 10. Gel-blocking is thereby reduced.

The swelling capacity (SC) of a superabsorbent material is the ratio of the volume of the superabsorbent material when wet to the volume in a dry state. The total swelling capacity (TSC) corresponds to the swelling capacity at saturation of the superabsorbent material.

Figure 4A:
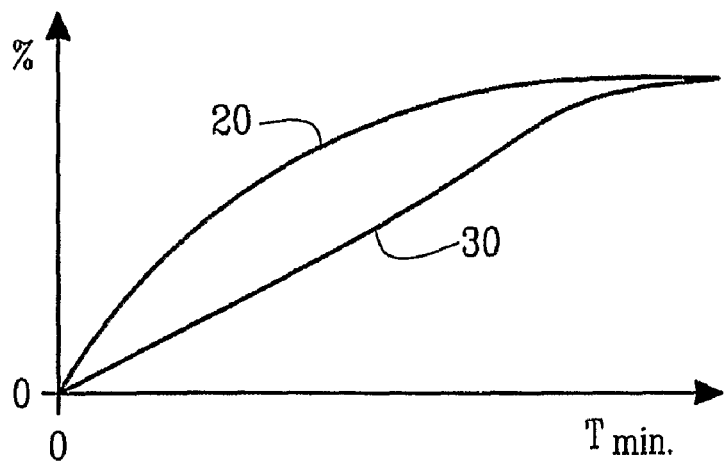
FIGS. 4a-c are schematic diagrams of the swelling (%) of two superabsorbent materials with time, according to three idealised embodiments of the invention.
Figure 4B:
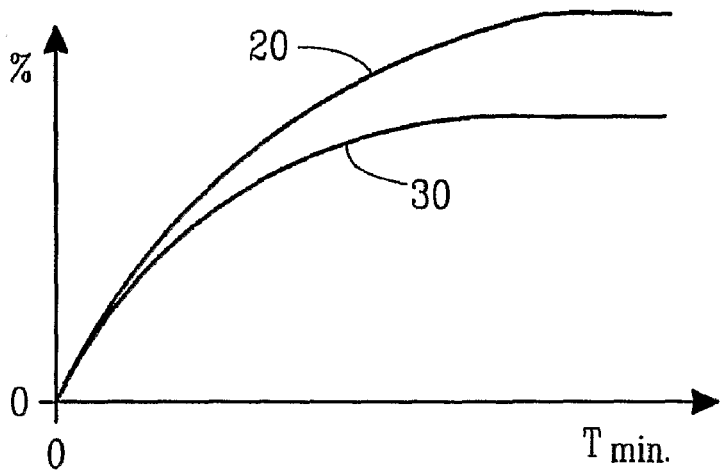
Figure 4C:
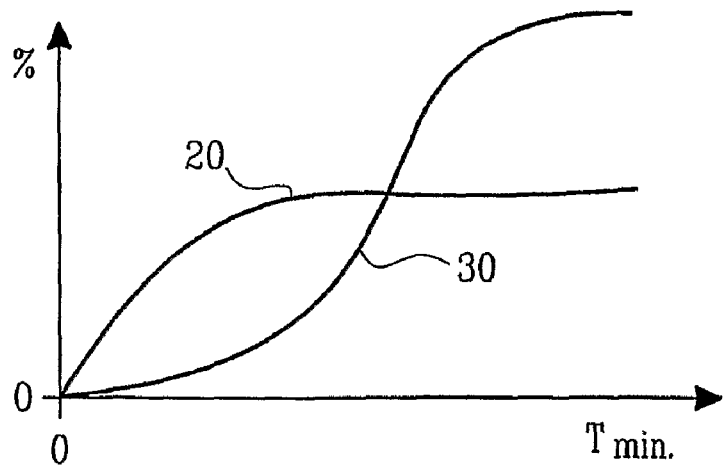

The swelling rate (SR) of an absorbent material is a measure of how quickly the absorbent material expands upon contact with liquid. It is expressed as the change in swelling capacity per unit time. With reference to FIGS. 4a-c, the swelling rate corresponds to the gradient of each curve.

FIGS. 4a-c illustrate idealised models of three different situations in which the superabsorbent materials 20, 30 have different swelling capacities and swelling rates.

In one embodiment, the swelling capacity (SC) of the first superabsorbent material (20) is greater than the swelling capacity (SC) of the second superabsorbent material (30) during liquid uptake, but the total swelling capacity (TSC) of each superabsorbent material may be the same. This is illustrated diagrammatically in FIG. 4a, which is a schematic graph of how two superabsorbent materials 20, 30 swell with time. As can be seen, the first superabsorbent material 20 has a higher swelling rate to begin with (higher gradient of the curve) and therefore expands first. This causes a high degree of curl in the superabsorbent fibre 10 upon contact with liquid. After a certain amount of time, the swelling of the first superabsorbent material reaches a constant value, while the second superabsorbent material 30 is still swelling. The superabsorbent fibre 10 straightens out again, as the swelling in the second superabsorbent material 30 increases. As both superabsorbent materials 20, 30 have the same TSC, they occupy the same volume when the superabsorbent fibre is completely saturated. This means that the curl which was established in the superabsorbent fibre 10 is removed, and the fibre 10 regains its uncurled (yet expanded) shape.

Thus superabsorbent fibres 10 in which the first superabsorbent material 20 and the second superabsorbent material 30 have the same total swelling capacity (TSC) yet different swelling rates (SR) will curl upon initial contact with liquid, providing a high-bulk, open structure. Upon continued contact with liquid, however, curl will be removed, and a low-bulk, more closed structure is obtained. Such materials are highly desirable in the field of absorbent hygiene articles, as they allow the production of thin articles which provide an open structure during liquid uptake, but which return to a closed structure upon complete saturation with liquid.

In another embodiment, the first superabsorbent material 20 and the second superabsorbent material 30 may have different total swelling capacities (TSC) yet similar swelling rates (SR). In other words, the difference in swelling capacity (SC) between the first and second superabsorbent materials 20, 30 is positive and increases with time. This is illustrated in FIG. 4b—the two materials 20, 30 swell at the same swelling rate, but stop swelling at different total swelling capacities. A superabsorbent fibre 10 comprising such materials may not curl to a large extent in the initial stages of liquid absorption, but will curl to a greater extent upon increased liquid absorption, when the problem of gel-blocking becomes more significant.

If the first superabsorbent material 20 and the second superabsorbent material 30 have both different total swelling capacities (TSC) and different swelling rates (SR), the swelling profile may be that illustrated in FIG. 4c. Upon contact with liquid, the two superabsorbent materials 20, 30 swell at different initial rates, leading to rapid curling of the superabsorbent fibre 10. However, upon continued contact with liquid, the superabsorbent materials 20, 30 may reach an equal swelling capacity in which the curl of the superabsorbent fibre 10 will be significantly reduced. Upon further contact with liquid, the curl of such a superabsorbent fibre will reverse, as the first superabsorbent material 20 becomes saturated while the second superabsorbent material 30 continues to absorb liquid.

The superabsorbent fibres 10 according to the invention can be manufactured by any suitable method for making fibres from polymeric materials. One possible method is coextrusion of the first and second superabsorbent materials 20, 30, while coating and laminating may also be used. To make the preferred embodiment of FIG. 3D, superabsorbent material may be coated on at least one side with cross-linking agent.

The multicomponent superabsorbent fibres 10 of the present invention may be used in an absorbent core 50 which forms the liquid-absorbing component of an absorbent article 100. Upon contact with liquid, the multicomponent superabsorbent fibres 10 of the invention swell and coil as described above and thereby provide the absorbent core 50 with an open structure. This open structure allows liquid to penetrate more freely into the core than in other materials, e.g. especially other superabsorbent fibres, and gel-blocking is thereby reduced. The absorbent core 50 may comprise other materials which are commonly-used in absorbent cores, such as e.g. pulp fibres, synthetic fibres, tissue webs or additional superabsorbent materials. Additionally, the multicomponent superabsorbent fibres 10 of the present invention may be used in acquisition or distribution layers within an absorbent article 100. As an alternative, the multicomponent superabsorbent fibres 10 of the present invention may be used in a topsheet 102 of an absorbent article 100.

Figure 5:
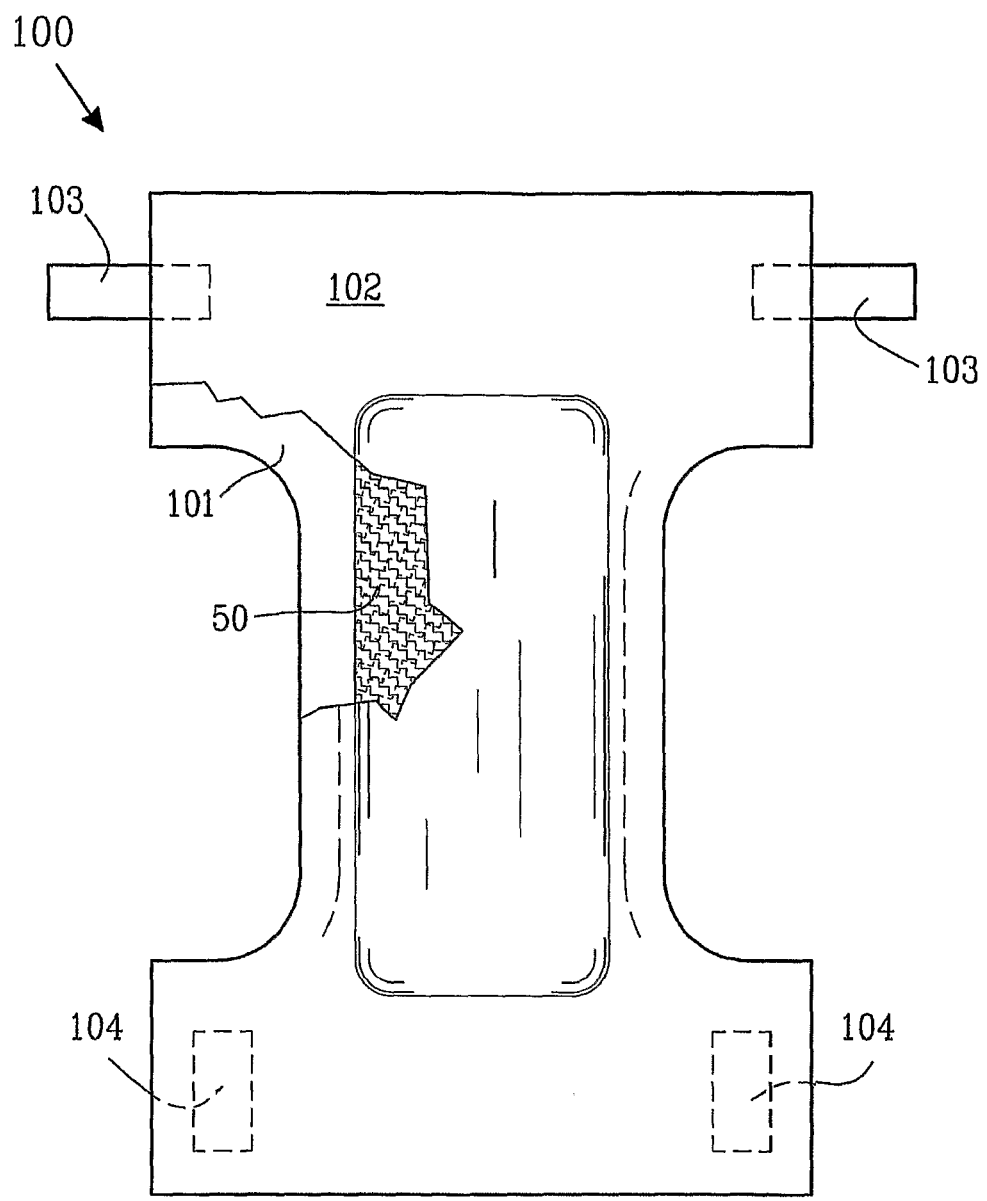
FIG. 5 shows an absorbent article according to the invention.

The absorbent core 50, acquisition/distribution layer or topsheet 102 comprising the superabsorbent fibres 10 of the present invention may in turn be comprised in an absorbent article 100, which is illustrated as a diaper in FIG. 5 but may also be any absorbent article such as a sanitary napkin, incontinence guard or panty liner. The diaper of FIG. 5 is shown from the user-facing side, with all elastic components fully outstretched. The absorbent article 100 of FIG. 5 comprises a topsheet 102 and a backsheet 101 located on opposite faces of the absorbent core 50, and fastening means 103, 104. The absorbent article 100 may also comprise one or more acquisition/distribution layers. The structure of absorbent articles which may comprise the superabsorbent fibres 10 of the invention, and methods for their manufacture are known to the person skilled in the art.

Description of Test Methods

Swelling Capacity

As mentioned above, the swelling capacity (SC) of a superabsorbent material is the ratio of the volume of the superabsorbent material when wet to the volume in a dry state. The superabsorbent fibre 10 can be observed under a microscope to determine whether it curls upon contact with liquid.

Determination of Swelling Capacity.

The Swelling Capacity of a superabsorbent material can be determined in a number of ways. One method is provided in Journal of Applied Polymer Science, vol 70, 817-829 (1998). Other methods are provided below, of which the Measuring Cylinder Method is preferred.

It is not usually possible to precisely measure the swelling capacity of the superabsorbent fibre 10 itself, as the component superabsorbent materials 20, 30 will contribute differently to the swelling. Instead, the swelling capacity of each superabsorbent material 20, 30 can be measured separately.

The weight unit in the present application is in grams if nothing else is stated.

Centrifuge Retention Capacity (CRC) Method.

Centrifuge Retention Capacity (CRC) is a standard method for measuring the liquid uptake of a superabsorbent material. The method corresponds to EDANA Standard Test WSP 241.2 (05). If nothing else is stated, the standard CRC according to the invention should be tested at 120 min (that is, the time intervals given in §6.6 and §8.9 of the WSP method should be 120 min). In addition, a sealed container should be used in the method rather than the dessicator specified in EDANA WSP 241.2 (05), §8.4.

All tests used in this application are made at 23° C.±2° C. and RH 50%±10% unless otherwise stated. The superabsorbents should be acclimatised in an atmosphere of 23° C.±2° C. and RH 50%±10% for 24 h before the tests are carried out.

Swelling Capacity Based on CRC

Essentially, the method describes first how a sample of superabsorbent material of known mass is exposed to liquid (usually 0.9 wt % sodium chloride solution) for a certain amount of time. The sample is removed and centrifuged. The CRC is the ratio of the weight of the liquid absorbed to the dry weight of the sample (in g/g). Knowing the density of the swelling liquid (0.9 wt % sodium chloride has a density of ca. 1 g/cm$^3$), and the density of the dry polymer it is possible to convert the CRC into a value for the swelling capacity in terms of volumes. The CRC can be measured at various time intervals so that a plot can be made of how the swelling capacity of each superabsorbent material varies with time.

Measuring Cylinder Method

Determination of SC is made in different steps:

Measure apparent density of dry superabsorbent

Measure specific density of wet superabsorbent (mass dry SAP per volume gel) i.e. after a CRC test.

The SC is the ratio between apparent density of the dry SAP and the specific density of the gel based on the mass of polymer in the gel.

Swelling Kinetics

The swelling kinetics of the swelling capacity, SC, as a function of time could be achieved if the EDANA method WSP 241.2 (05) is performed with different residence times of the superabsorbents in the liquid (the sodium chloride solution). The WSP method should be followed as set out above except for the change in residence time of the superabsorbents.

The preferred residence times, t, to be used are 1, 5, 10, 20, 30, 60 and 120 minutes. The result of the EDANA method WSP 241.2 (05) is the centrifuge retention capacity, CRC.

For the cylinder method the following procedures should be used: The CRC could be used in the estimation of kinetics. The SC value is estimated as SC at 120 minutes divided by the CRC, at 120 minutes multiplied by the CRC at the actual time: SC(t)=CRC(t)*(SC(120 min)/CRC(120 min)).

As the SC data are to be compared for the different qualities of super absorbents used in the invention the test should be made with the same particle size, e.g. a fraction of 200-300 micrometers. The data for both superabsorbents are plotted in a diagram, SC vs. time, and an interpolation is made between the data, for each superabsorbent. From the diagram the SC(t) for the two super absorbents could be compared.

No Exchange Between SAPs

Suitably, the CRC value should be the same for each superabsorbent, whether they are tested separately or together in the same bath for two hours. In other words, there should be no ion exchange between the superabsorbents. In this way, the swelling capacity (SC) of each superabsorbent polymer 20, 30 remains the same when the polymers 20,30 are laid together in a fibre and the SC ratio should be maintained when both superabsorbent polymers are laid together in a fibre.

Apparent Density of Dry Superabsorbent (Archimedes Test)

Use a measuring cylinder of 250 ml graded in $\leqq 2$ ml intervals with the scale being at least 20 cm high in order to get the required resolution for the measurement. Weigh the cylinder. Record the weight, $m_{cyl}$. Add 180 ml of super absorbents, including pores, to the cylinder. Record the weight, $m_{SAP+cyl}$. Add 100% ethanol pro analyst up to the level of 250 ml in the cylinder. If there seems to be air entrapped use an ultrasonic bath to get rid of it. Just put enough liquid in the bath and let the ultra sonic waves work on the sample for some 15 seconds, or until the air bubbles have disappeared. Fill up with liquid to 250 ml, measured at the surface of the liquid, as the liquid level may get lowered when air leaves the sample. If the cylinder is left for some time before the final readings are made, make sure that the cylinder is properly sealed so that no liquid disappears. Record the weight of the cylinder, gel and liquid, $m_{tot}$.

The apparent density, $\rho_a$, is:

$$\rho_a = \frac{m_{SAP+cyl} - m_{cyl}}{(250 - (m_{tot} - m_{SAP+cyl})/\rho_{Ethanol})} [\text{g dry polymer/cm}^3 \text{ dry polymer}]$$

The density of the ethanol, $\rho_{ethanol}$, should be used that is 0.79 g/cm$^3$ at 23° C.

Specific Density of Wet Superabsorbent

Use a glass measuring cylinder of 250 ml graded in $\leqq 2$ ml intervals with the scale being at least 20 cm high in order to get the required resolution for the measurements, preferably the same cylinder used in the former tests after it has been cleaned and dried properly. Weigh the cylinder and record the weight, $m_{cyl}$. Use the CRC method described above to produce superabsorbent gel. After centrifugation and weighing in the CRC test, the bags are collected. If more than one set of bags from a CRC test is needed, then store the centrifuged samples in a tight-sealed container, meanwhile producing more gel. Approximately 180 ml of the gel, including pores, i.e. about 100 g of gel is needed. Open up the sealed bag and take out the gel. Add the gel directly to the cylinder. Note the weight of the gel, $m_{gel}$, i.e. the total mass of the cylinder and gel minus the weight of the cylinder, $m_{cyl}$. Add liquid, i.e. the same 0.9 w-% NaCl solution used for the CRC test, to the measuring cylinder. Fill up the cylinder to 250 ml. If there seems to be entrapped air, use an ultrasonic bath to get rid of it—place the cylinder and contents in the ultrasonic bath for some 15 seconds, or until the air bubbles disappear. Fill up with liquid to 250 ml, measured at the surface of the liquid, as the liquid level may fall when air leaves the sample. If the cylinder is left for some time before the final readings are made, make sure that the cylinder is properly sealed so that no liquid disappears. Record the weight of the cylinder, gel and liquid, $m_{tot}$. The density of the wet gel $\rho_{gel}$ is calculated per mass of dry superabsorbent:

$$\rho_{gel} = \frac{m_{gel}[g]}{(CRC+1)(250 - (m_{tot} - m_{cyl} - m_{gel})/\rho_{NaCl})} [\text{g dry polymer/cm}^3 \text{ gel}]$$

The density of the 0.9 wt. % NaCl solution $\rho_{NaCl}$ that should be used is 1.01 g/cm$^3$ at 23° C.

Then calculate SC:

$$SC = \frac{\rho_a}{\rho_{gel}} [\text{cm}^3 \text{ gel/cm}^3 \text{ dry polymer}]$$

Curvature

Figure 6:
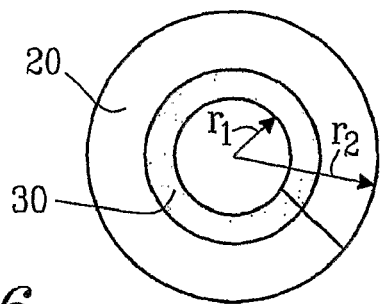
FIG. 6 illustrates the basis for a mathematical model used to calculate the radius of curvature of a curled fibre.

The degree by which a fibre curls can be determined by the "radius of curvature". A fibre with a smaller radius of curvature will have a tighter curl. After swelling, an ideally-curled superabsorbent fibre will have a helix-shape, and when one looks down the axis, one sees a circle with an inner radius of curvature $r_1$ and an outer radius of curvature $r_2$. This is illustrated in FIG. 6.

EXAMPLES

Polymer A 25 weight % sodium polyacrylate was neutralised to 100 mol %. It was then cross-linked with 1 mol % MBA (N,N'-methylene bisacrylamide). Initiated with 0.1 mol % VA-044 (2,2'-azobis[2-(2-imidazonli-2-yl)propane]dihydrochloride) at 50° C. Polymer A had a CRC of 20 g/g, as tested in 0.9% NaCl solution according to the EDANA method WSP 241.2 (05) for 120 minutes.

Polymer B 25 weight % sodium polyacrylate was neutralised to 100 mol %. It was then cross-linked with 0.1 mol % MBA (N,N'-methylene bisacrylamide). Initiated with 0.1 mol % VA-O44 (2,2'-azobis[2-(2-imidazonli-2-yl)propane] dihydrochloride) at 50° C. Polymer B had a CRC of 50g/g, as tested in 0.9% NaCl solution according to the EDANA method WSP 241.2 (05) for 120 minutes.

According to the methods above, polymer A swells to 20 g/g and polymer B swells to 50 g/g. Assuming that the polymers have similar densities, the volume ratio of the swollen gels is about 50/20=2.5. This implies that the ratio in length scales is $\sqrt[3]{2.5} \approx 1.4$ between the two gels. That is, for a curled fibre according to the invention, $r_2/r_1$ should be at least 1.03, preferably at least 1.1, more preferably at least 1.2 and most preferably at least 1.4 along at least 20%, such as at least 50% or at least 75% of the total length of the fibre. Before contact with liquid the superabsorbent fibres 10 should have a radius of curvature ratio $r_2/r_1$ of at most 1.

The present invention should not be limited by the embodiments described herein and the enclosed Figures. Rather, the scope of protection is defined according to the appended claims.

The invention claimed is:

1. A multicomponent superabsorbent fibre, said superabsorbent fibre having a length direction and a cross-direction, said superabsorbent fibre comprising a first superabsorbent material and a second superabsorbent material,
   wherein, in at least a part of the length direction of the superabsorbent fibre, the first superabsorbent material and the second superabsorbent material are located side-by-side in the cross-direction of the superabsorbent fibre,
   wherein
   the first and second superabsorbent materials are selected such that at a given point during their swelling, the swelling capacity of the first superabsorbent material is greater than the swelling capacity of the second superabsorbent material so that the superabsorbent fibre curls upon contact with liquid;
   provided that the multicomponent superabsorbent fibre does not comprise one or more first fibres comprising an acidic water-absorbent resin and one or more second fibres comprising a basic water-absorbent resin; and
   wherein the first superabsorbent material and the second superabsorbent material comprise the same superabsorbent polymer, wherein the superabsorbent polymer in the second superabsorbent material has a higher cross-linking density than the superabsorbent polymer in the first superabsorbent material.

2. The superabsorbent fibre according to claim 1, which is a bicomponent fibre consisting of the first superabsorbent material and the second superabsorbent material.

3. The superabsorbent fibre according to claim 1, wherein the first superabsorbent material and the second superabsorbent material have the same total swelling capacity yet different swelling rates.

4. The superabsorbent fibre according to claim 1, wherein the first superabsorbent material has a total swelling capacity which is at least 1.1 times greater than that of the second superabsorbent material.

5. The superabsorbent fibre according to claim 1, wherein the first and second superabsorbent materials are arranged such that there is at least one plane or axis of asymmetry in the swelling capacity in the length direction of the superabsorbent fibre.

6. The superabsorbent fibre according to claim 1, wherein the swelling capacity of each the superabsorbent material remains the same when the materials are laid together in a fibre.

7. An absorbent core comprising a plurality of the multicomponent superabsorbent fibre of claim 1.

8. An absorbent article comprising the absorbent core according to claim 7.

9. A method for reducing gel-blocking in a multicomponent superabsorbent fibre, said method comprising;
   providing a multicomponent superabsorbent fibre having a length direction and a cross-direction, said superabsorbent fibre comprising a first superabsorbent material and a second superabsorbent material,
   wherein in at least a part of the length direction of the fibre, the first superabsorbent material and the second superabsorbent material are located side-by-side in the cross-direction of the superabsorbent fibre,
   wherein the first and second superabsorbent materials are selected such that at a given point during their swelling, the swelling capacity of the first superabsorbent material is greater than the swelling capacity of the second superabsorbent material;
   provided that the multicomponent superabsorbent fibre does not comprise one or more first fibres comprising an acidic water-absorbent resin and one or more second fibres comprising a basic water-absorbent resin;
   wherein the first superabsorbent material and the second superabsorbent material comprise the same superabsorbent polymer, wherein the superabsorbent polymer in the second superabsorbent material has a higher cross-linking density than the superabsorbent polymer in the first superabsorbent material;
   and exposing the superabsorbent fibre to liquid, wherein at a given point during their swelling, the swelling capacity of the first superabsorbent material is greater than the swelling capacity of the second superabsorbent material, causing the bicomponent superabsorbent fibre to curl.

10. The superabsorbent fibre according to claim 4, wherein the first superabsorbent material has a total swelling capacity which is at least 3 times greater than that of the second superabsorbent material.

11. The superabsorbent fibre according to claim 1, wherein the first superabsorbent material and the second superabsorbent material are located side-by-side in the cross-direction of the superabsorbent fibre, in only a part of the length direction of the superabsorbent fibre.

* * * * *